US012624326B2

(12) United States Patent
Maier et al.

(10) Patent No.: US 12,624,326 B2
(45) Date of Patent: May 12, 2026

(54) SENSOR RECEPTACLE FOR USING A CONVENTIONAL SENSOR WITH A SINGLE-USE BIOREACTOR WHILE MAINTAINING THE STERILITY OF THE SINGLE-USE BIOREACTOR

(71) Applicant: Mettler-Toledo GmbH, Greifensee (CH)

(72) Inventors: Anne Maier, Schlieren (CH); Stefan Bardeck, Oberengstringen (CN)

(73) Assignee: Mettler-Toledo GmbH, Greifensee (CH)

( * ) Notice: Subject to any disclaimer, the term of this patent is extended or adjusted under 35 U.S.C. 154(b) by 749 days.

(21) Appl. No.: 17/996,029

(22) PCT Filed: Apr. 8, 2021

(86) PCT No.: PCT/EP2021/059149
§ 371 (c)(1),
(2) Date: Oct. 12, 2022

(87) PCT Pub. No.: WO2021/209303
PCT Pub. Date: Oct. 21, 2021

(65) Prior Publication Data
US 2023/0212494 A1     Jul. 6, 2023

(30) Foreign Application Priority Data

Apr. 15, 2020     (DE) ......................... 102020110349.2

(51) Int. Cl.
*C12M 3/00*          (2006.01)
*B01L 3/00*          (2006.01)
(Continued)

(52) U.S. Cl.
CPC ............ *C12M 23/28* (2013.01); *C12M 23/26* (2013.01); *C12M 23/34* (2013.01); *C12M 23/46* (2013.01); *C12M 41/30* (2013.01)

(58) Field of Classification Search
CPC .............................. C12M 41/00; C12M 23/26
See application file for complete search history.

(56)                    References Cited

U.S. PATENT DOCUMENTS 7,832,922 B2    11/2010  Schoeb
8,828,202 B2     9/2014  Feng
(Continued)

FOREIGN PATENT DOCUMENTS

AU          732530 B2    4/2001
DE        2052103 A1    4/1972
(Continued)

*Primary Examiner* — Nathan A Bowers
(74) *Attorney, Agent, or Firm* — Standley Law Group LLP; Jeffrey S. Standley; Adam J. Smith

(57)                    ABSTRACT

A bioreactor system (1) has a pre-sterilized single-use bioreactor (2) with a reactor wall (20) surrounding an interior chamber (21) that receives a fluid medium (M). A sensor (3) for detecting an analyte in the medium has a sensor housing (30) with an outside thread (31) and a sensor shaft (32), a distal end portion (33) of which has an end face (34) with a region (35) permeable to the analyte. A sensor receptacle (4) connected to the reactor wall receives the sensor, to maintain the sterility of the single-use bioreactor. A circumferential flange (40) fixes the sensor receptacle to the reactor wall. The flange has an inside thread (42) that receives the outside thread. A wall (43) of the sensor receptacle is connected to the flange, and together with the sensor shaft, protrudes into the interior chamber, separating the sensor from the interior chamber.

15 Claims, 3 Drawing Sheets

(51) Int. Cl.
    *C12M 1/00*          (2006.01)
    *C12M 1/34*          (2006.01)

(56)              References Cited

U.S. PATENT DOCUMENTS

| | | | |
|---|---|---|---|
| 8,900,855 | B2 | 12/2014 | Feng et al. |
| 9,103,703 | B2 * | 8/2015 | Baumfalk ............... C21C 5/527 |
| 9,410,626 | B2 | 8/2016 | Feltham |
| 10,233,417 | B2 * | 3/2019 | Keitel .................... C12M 41/02 |
| 11,339,416 | B2 | 5/2022 | Eubisch et al. |
| 2007/0185472 | A1 * | 8/2007 | Baumfalk ............. A61M 39/10 |
| | | | 604/533 |
| 2010/0035337 | A1 | 2/2010 | Bahnemann et al. |
| 2011/0111489 | A1 | 5/2011 | Beese et al. |
| 2019/0264163 | A1 | 8/2019 | Dierker et al. |
| 2019/0309253 | A1 | 10/2019 | Ott et al. |
| 2020/0208094 | A1 | 7/2020 | Höhse et al. |
| 2020/0362292 | A1 | 11/2020 | Hoehse et al. |

FOREIGN PATENT DOCUMENTS

| | | | | |
|---|---|---|---|---|
| DE | 102013015106 | A1 | 3/2015 | |
| EP | 2251407 | B1 | 6/2016 | |
| EP | 4339603 | A2 * | 3/2024 | ........... G01N 27/283 |
| WO | WO-2010017519 | A1 * | 2/2010 | ........... A61M 39/18 |

* cited by examiner

SENSOR RECEPTACLE FOR USING A CONVENTIONAL SENSOR WITH A SINGLE-USE BIOREACTOR WHILE MAINTAINING THE STERILITY OF THE SINGLE-USE BIOREACTOR

The invention relates to a bioreactor system comprising a single-use bioreactor and a sensor for measuring an analyte contained in a medium located in an interior chamber of the single-use bioreactor. Furthermore, the invention relates to a method which is carried out using the bioreactor system and to a sensor receptacle with which a single-use bioreactor can be equipped in such a way that said single-use bioreactor can be used together with a conventional sensor without breaking the sterility of the single-use bioreactor.

A single-use bioreactor is a bioreactor that is only used for carrying out a single process and is then disposed of. The use of a new, pre-sterilized single-use bioreactor in each case for each individual process makes it possible to reduce the risk of contamination, wherein, furthermore, the effort of cleaning the bioreactor is eliminated. Single-use bioreactors are also referred to as disposable bioreactors.

Single-use bioreactors are becoming increasingly important as process reactors, so it is desirable to be able to equip such a reactor with a sensor so that an analyte contained in a medium located in the single-use bioreactor is measurable.

Therefore, it is the object of the invention to provide a bioreactor system which has a single-use bioreactor which permits the use of a sensor for measuring an analyte present in the single-use bioreactor in a simple and efficient manner.

This object is achieved by a single-use bioreactor system with the features of claim 1. Advantageous configurations of the single-use bioreactor system are specified in the corresponding dependent claims and are described below.

According to claim 1, there is disclosed a bioreactor system, comprising:

- a pre-sterilized single-use bioreactor having a reactor wall which surrounds an interior chamber of the single-use bioreactor, the interior chamber being designed to receive a fluid medium;
- a separate sensor being designed to detect a gaseous analyte present in the medium or an analyte dissolved in the medium, the sensor having a sensor housing with a fastening region (e.g., in the form of an outside thread) and a sensor shaft, the sensor shaft having a distal end portion with an end face which has a region which is permeable to the analyte for passing through the analyte, in such a way that in particular the analyte in the sensor housing can be measured by respective measuring unit or sensor system;
- a sensor receptacle connected fluid-tight to the reactor wall and designed to receive the sensor, such that the sterility of the single-use bioreactor is maintained, the sensor receptacle having a circumferential flange via which the sensor receptacle is fixed to the reactor wall, the flange having a fastening region (e.g., an inside thread at a circumferential inner side of the flange) configured to be connected in a detachable force-fitting and/or form-fitting manner with the fastening region of the sensor housing (e.g., the outside thread of the sensor housing can be screwed into the inside thread of the flange), and the sensor receptacle having a wall connected to the flange which wall, together with the sensor shaft, protrudes into the interior chamber of the single-use bioreactor when the sensor is arranged in the sensor receptacle and is connected to the fastening region of the sensor receptacle or the flange by means of its fastening region as intended, wherein the wall of the sensor receptacle is designed in such a way, that the end face of the distal end portion of the sensor shaft bears against a portion of the wall of the sensor receptacle when the fastening region of the sensor is connected to the fastening region of the flange as intended, wherein at least said portion of the wall of the sensor receptacle is formed from a flexible membrane, which is permeable to the analyte so that the analyte can pass through the flexible membrane to the permeable region of the sensor.

Due to the sensor receptacle, the invention advantageously allows the use of an unmodified standard sensor as is used also in multi-use bioreactors made of glass or stainless steel. In this case, the entire sensor as such—in contrast to the single-use bioreactor—is reusable on account of the detachable connection to the sensor receptacle and the arrangement outside the interior chamber of the single-use bioreactor, so that no complicated pre-sterilization or autoclaving of the sensor (completely or in parts) or no storage of the sensor as a whole or in parts together with the single-use bioreactor is required. The present invention is specifically designed for single-use bioreactors (see above). However, according to a further aspect of the invention, it is also conceivable, instead of a single-use bioreactor, to use a bioreactor provided, for example, for a small number of uses (e.g., two to three cycles).

If the sensor is correctly arranged in the sensor receptacle, the sensor shaft protrudes with the distal end portion into the interior chamber of the single-use bioreactor and is, in this case, surrounded by the wall of the sensor receptacle, which separates the sensor completely from the interior chamber of the single-use bioreactor, which ensures the sterility of the single-use bioreactor. A proximal end portion of the sensor housing opposite the distal end portion preferably protrudes out of the sensor receptacle and can have an electrical connector for electrical contacting the sensor. The proximal end portion is arranged closer to the user and can be manually gripped by the user in order to screw the sensor into the sensor receptacle or to connect it to it or to remove it therefrom.

According to an embodiment of the invention, the sensor shaft of the sensor has an elongated shape. In this case, the sensor shaft can extend along a longitudinal axis of the sensor or of the sensor housing. Alternatively, the sensor shaft can be arranged at an angle to an adjacent section of the sensor housing.

Furthermore, according to one embodiment, the sensor is designed to measure a concentration of the analyte in the medium.

According to one embodiment of the invention, the flange is integrally connected to the reactor wall (e.g. via an adhesive connection or a welded connection). Furthermore, the flange can alternatively be connected to the reactor wall via a force-fitting connection (e.g. by a screw or crimp connection).

Furthermore, the flange can be formed from a plastic or from a metal alloy.

According to one embodiment of the invention, it is provided that the sensor receptacle is configured in such a way that the portion of the wall of the sensor receptacle or the flexible membrane is pre-stressed against the end face of the distal end portion of the sensor shaft when the sensor is arranged in the sensor receptacle and the outside thread of the sensor housing is screwed into the inside thread of the sensor receptacle as intended or the fastening region of the sensor housing is detachably connected to the fastening region of the flange as intended.

Furthermore, according to one embodiment of the invention, it is provided that the wall of the sensor receptacle is designed to be expandable such that the wall is expanded in a direction in which the sensor shaft can be inserted into the sensor receptacle when the sensor is inserted into the sensor receptacle and the outside thread of the sensor housing is screwed into the inside thread of the sensor receptacle as intended (or the fastening region of the sensor receptacle is detachably connected to the fastening region of the flange as intended). Said direction coincides in particular with the longitudinal axis of the sensor shaft.

According to one embodiment of the invention, it can furthermore be provided that the wall is formed completely by the flexible membrane, wherein in particular said portion of the wall which contacts the end face of the sensor shaft can form an end portion of the wall (in particular on account of the expansion of the wall by the sensor shaft).

According to an alternative embodiment of the invention, it is provided that the wall of the sensor receptacle has a rigid wall portion which extends in a circumferential direction and is connected to said portion of the wall which is formed by the flexible membrane and preferably forms an end portion of the wall of the sensor receptacle. According to one embodiment, it is furthermore provided that the rigid wall portion is of cylindrical design.

Furthermore, according to one embodiment of the invention, it is provided that the flexible membrane is formed from one of the following materials or comprises one of the following materials: a polymer, an organic polymer, an inorganic polymer, a poly(organo)siloxane.

According to a further embodiment of the bioreactor system, it is provided that the analyte is selected from the group consisting of: oxygen, $CO_2$, $SO_2$, $H_2O_2$, $NO_x$, a halogenated hydrocarbon (i.e. a hydrocarbon in which at least one hydrogen atom has been replaced by one of the halogens fluorine, chlorine, bromine or iodine).

Furthermore, according to a preferred embodiment of the invention, it is provided that the sensor shaft has a sleeve at the distal end portion of the sensor shaft, on which sleeve the region of the sensor permeable to the analyte is fixed or which is designed for fixing the permeable region to the sensor, wherein the sleeve can be detachably connected to a base of the sensor shaft. For this purpose, the sleeve can have an inside thread which can be screwed into an outside thread of the base of the sensor shaft. The sleeve can have further functional components for detecting the analyte.

Furthermore, according to one embodiment of the invention, it is provided that the reactor wall is designed to be at least partially rigid or fixed. Furthermore, the reactor wall can be designed to be flexible. Thus, the reactor wall can, for example, be designed to form a bag-like container. The reactor wall can in particular be formed from a transparent or a translucent material. Preferably, the reactor wall is formed from a suitable polymer.

In principle, the single-use bioreactor can be a stirred single-use bioreactor which has at least one stirring element for mixing the medium, wherein the at least one stirring element is likewise designed as a single-use component and is already integrated and pre-sterilized in the single-use bioreactor. When using the single-use bioreactor, the at least one stirring element can be coupled mechanically or magnetically to a stirring motor. Furthermore, the single-use bioreactor can also be a seesawed single-use bioreactor or a single-use bioreactor shaken from the outside, which does not have any further mechanical internals for mixing the medium.

Preferably, the analyte according to one embodiment is oxygen dissolved in the medium. In this case, the sensor can be designed, for example, as an optochemical sensor for measuring dissolved oxygen. In this case, the permeable or oxygen-permeable region of the sensor shaft can be formed from a poly(organo)siloxane, an optical layer with a chromophore adjoining the permeable region. Both the permeable region as well as the optical layer can form components of the sleeve or can be fixed at the sleeve.

The sensor can furthermore be designed to illuminate the optical layer with green light and in the process to excite it, so that the chromophores emit fluorescent light when they return to their ground state. The mean time to return to the ground state is referred to as fluorescence lifetime. When oxygen diffused through the permeable region of the sensor collides with chromophores in the excited state, the energy of the chromophores can be transferred to the oxygen molecules (so-called dynamic quenching). The fluorescence lifetime of the excited state of the chromophores is then shortened. The shortening is dependent on the oxygen concentration.

The fluorescence lifetime can be measured by means of phase shift. For this purpose, the excitation light is modulated. If no oxygen is present in the environment of the chromophore, the phase shift of the light emitted by the chromophore relative to the excitation light is large (long fluorescence lifetime of the chromophore). The fluorescence lifetime, and thus the phase shift, decreases with increasing oxygen concentration and can therefore be used to calculate the oxygen concentration. The oxygen concentration can therefore be determined by the sensor and can, for example, be transmitted in digital form to a transmitter of the sensor.

According to a further preferred embodiment, the analyte is $CO_2$ dissolved in the medium. In this case, the sensor is preferably a sensor for measuring dissolved $CO_2$, for example, using potentiometric principles (Severinghaus). In this case, the sensor can have a pH electrode which is surrounded by a pH-sensitive glass. $CO_2$ from the medium stored in the single-use bioreactor can in this case diffuse through the permeable region of the sensor shaft into a $CO_2$ electrolyte located between the permeable region and the pH electrode until the same $CO_2$ partial pressure (equilibrium) has been established on both sides. The diffused $CO_2$ reacts with the electrolyte to form bicarbonate ions as well as H+ ions: $CO_2 + H_2O \leftrightarrow HCO_3^- + H^+$.

The change in H+ ion activity in the electrolyte can be measured with the pH electrode. Using the pH and the simultaneously measured temperature, the $CO_2$ partial pressure can be determined by the sensor.

In a $CO_2$ sensor, the sleeve may be designed to fix and/or surround the permeable region at the pH electrode. In this case, the sleeve can have a passage opening at one end of the sleeve, via which the permeable region is accessible for the analyte. Due to the end-face opening, the sleeve can also be referred to as a coupling sleeve.

According to a further embodiment, the sensor can also be designed to measure dissolved $CO_2$ optochemically. In this case, the sensor can have a $CO_2$-sensitive chromophore.

As already explained, the fastening region of the sensor housing can be an outside thread of the sensor housing, wherein the fastening region of the flange can be an inside thread which can be provided on a circumferential inner side of the flange, wherein in particular the outside thread can be screwed into the inside thread for producing the detachable force-fitting and/or form-fitting connection. Furthermore, the fastening regions on both sides can also implement other detachable force-fitting and/or form-fitting connections, for example, a bayonet connection, a snap-on connection etc.

A further aspect of the invention relates to a method for measuring an analyte in a medium using a bioreactor system according to the invention, comprising the steps of:

providing the pre-sterilized single-use bioreactor, arranging the separate sensor in the sensor receptacle, wherein the outside thread of the sensor is screwed into the inside thread of the sensor receptacle (or the fastening region of the sensor housing is detachably connected as intended to the fastening region of the flange) in such a way that the end face of the distal end portion of the sensor shaft bears against the portion of the wall of the sensor receptacle, and measuring a concentration of the analyte by means of the sensor.

The sensor is preferably arranged unchanged in the sensor receptacle without prior modification. The invention therefore advantageously makes it possible to use already available standard sensors which can readily be used with the sensor receptacle according to the invention. For this purpose, no changes need to be made to the individual sensor.

In particular, the single-use bioreactor is disposed of after one use, wherein the sensor is removed beforehand from the sensor receptacle for the purpose of reusing said sensor.

According to a further aspect of the invention, a sensor receptacle is disclosed which is configured to receive a sensor for a single-use bioreactor such that an interior chamber of the single-use bioreactor is separated from the sensor and a sterile state of the single-use bioreactor is maintained, wherein the sensor receptacle comprises:

a circumferential flange designed to be fixed to a reactor wall of the bioreactor in such a way that the sensor receptacle is connected to the reactor wall in a fluid-tight manner, the flange having a fastening region (e.g., an inside thread on a circumferential inner side of the flange) which can be detachably connected to a fastening region of the sensor housing of the sensor (e.g. an outside thread of the sensor housing), a wall of the sensor receptacle, which wall is connected to the flange and which is set up and provided for separating the sensor from the interior chamber of the single-use bioreactor, wherein the wall is designed in such a way that an end face of a distal end portion of a sensor shaft of the sensor bears against a portion of the wall of the sensor receptacle, when the sensor is arranged in the sensor receptacle and the fastening region of the sensor is connected to the fastening region of the flange as intended (e.g. when the outside thread is screwed into the internal thread), wherein at least the portion of the wall of the sensor receptacle is formed from a flexible membrane which is permeable to an analyte to be measured by means of the sensor, which analyte is contained in a medium in the interior chamber of the single-use bioreactor, in such a way that the analyte can pass through the flexible membrane to a region, permeable to the analyte, of the end face of the distal end portion of the sensor shaft.

According to one embodiment of the sensor receptacle, the flange is designed to be integrally connected to the reactor wall (e.g. via an adhesive connection or a welded connection). Furthermore, alternatively, it can also be provided that the flange can be connected to the reactor wall via a force-fitting connection (e.g. by a screw or crimp connection).

The sensor receptacle can furthermore be developed by the features or embodiments set forth further above in connection with the bioreactor system.

Embodiments of the invention and further features and advantages of the invention are explained below with reference to the figures, which represent preferred embodiments of the invention. In the figures.

Figure 1:
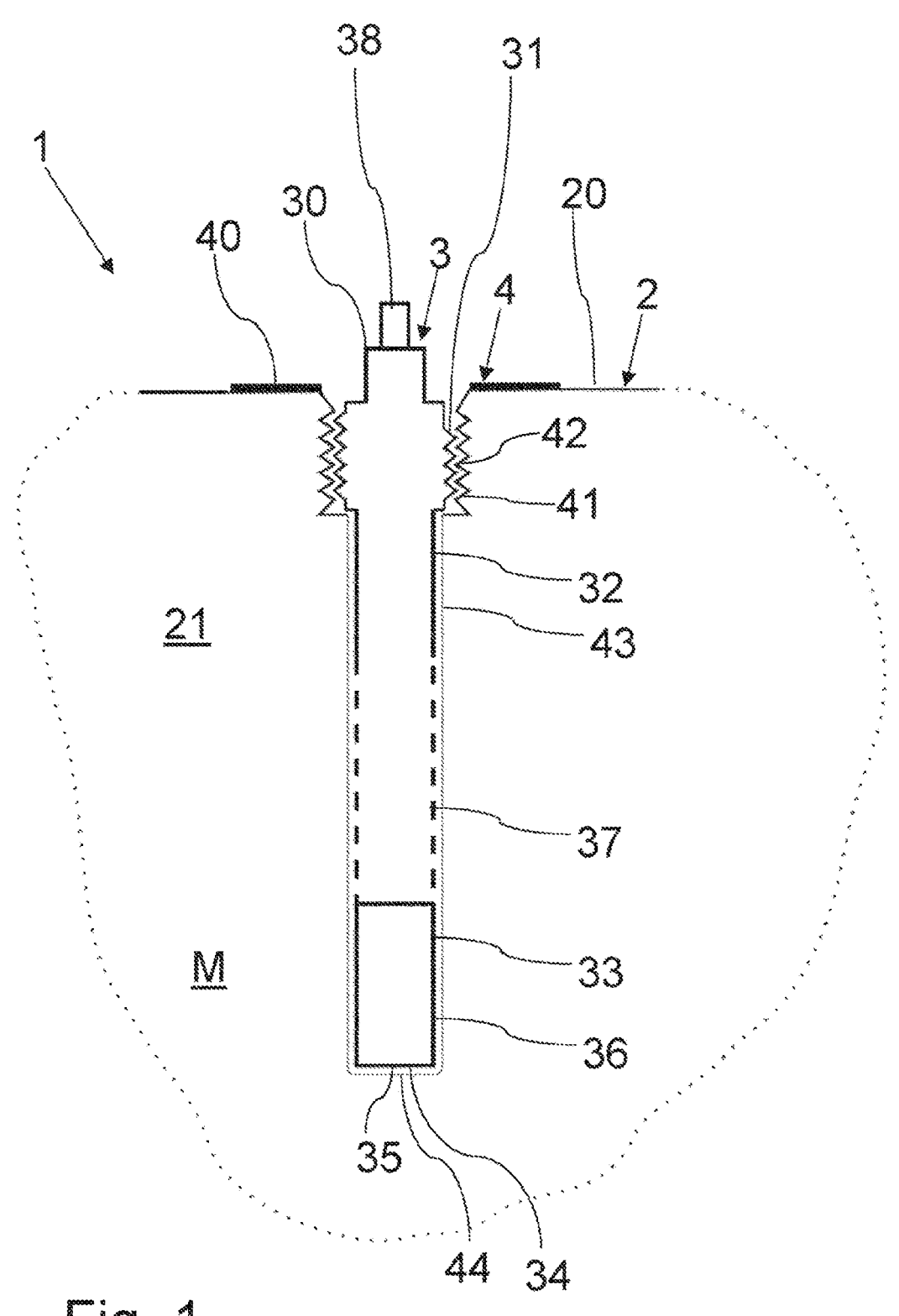
FIG. 1 shows a schematic sectional illustration of an embodiment of a reactor system according to the invention.

FIG. 1 shows a sectional illustration of an embodiment of a bioreactor system 1 according to the invention. System 1 has a pre-sterilized single-use bioreactor 2 which surrounds an interior chamber 21 into which a medium M can be filled. The medium M can be any and all possible substances or mixtures of substances that can be processed in a single-use bioreactor 2, in particular culture media. The single-use bioreactor 2 has a reactor wall 20 which surrounds interior chamber 21 and can form a fixed container. However, reactor wall 20 can alternatively also be of flexible design in such a way that the single-use bioreactor 2 forms, for example, a bag-shaped container.

System 1 furthermore has a sensor 3, which is preferably a conventional, in particular sterilizable or autoclavable sensor 3. Sensor 3 can in particular be one of the sensors 3 described above, in particular an optochemical sensor 3 for determining a concentration of dissolved oxygen or dissolved $CO_2$ in medium M or another sensor 3 for determining a concentration of dissolved $O_2$ or dissolved $CO_2$ in the medium M. However, other sensors 3 are also conceivable.

Sensor 3 preferably has an elongated and fixed sensor housing 30 with an outside thread 31 at a proximal end portion of the sensor housing 30, and a sensor shaft 32 which forms a distal end portion 33 of the sensor housing 30, in which a sensor system is arranged that is sensitive to the respective analyte (e.g., dissolved oxygen or dissolved $CO_2$). The length of sensor shaft 32 can be adapted to the respective use or installation situation. Sensor housing 30 can also have analysis electronics and a transmitter for transmitting an output signal of sensor 3 which is indicative of the respective measured variable. Furthermore, an electrical connector 38 for electrically contacting sensor 3 can be formed at the proximal end of sensor 3, so that the output signal can be output or forwarded, optionally via a cable connection.

The distal end portion 33 of the sensor shaft 32, which is designed to dip into interior chamber 21 of the single-use bioreactor 2—with the interposition of a separating layer 43—has an end face 34, which has a permeable region 35, which is permeable to the analyte to be measured in medium M. The analyte can therefore enter into an interior chamber of the sensor 3 surrounded by the distal end portion 33 of the sensor shaft 32 through the permeable region 35 and can there (e.g. by means of a sensitive or optical layer) be detected and optionally quantitatively determined by means of the sensor system.

To use the sensor 3 with the single-use bioreactor 2, the latter has a sensor receptacle 4 which provides the separation layer 43 mentioned at the outset in such a way that the sensor 3 can be used with the single-use bioreactor 2 without impairing its sterile state, i.e. without contaminating the medium M located in the interior chamber 21. The sensor receptacle 4 is designed in particular in such a way that sensor 3 as a whole and preferably without a further reconfiguration or modification can be positioned in the sensor receptacle 4 and is immediately ready for operation there.

Sensor receptacle 4 can be provided as a separate unit. In this case, it is advantageous for the sensor receptacle 4 to be connected to the reactor wall 20 of the single-use bioreactor only via a single element. This is a flange 40 which forms a central opening for inserting sensor 3. Flange 40 is or can be connected to the reactor wall 20 in a fluid-tight manner via all suitable types of connection. These connections include both integral connections and force-fitting connections.

For fixing sensor 3 in the sensor receptacle 4, flange 40 has, on an inner side 41 of flange 40, an inside thread 42 into which outside thread 31 of sensor 3 can be screwed. Sensor receptacle 4 furthermore has a wall 43 which forms said separating layer 43 and is configured, together with sensor shaft 32, to protrude into interior chamber 21 of the single-use bioreactor 2, wherein wall 43 surrounds sensor shaft 32 and completely isolates it from medium M or from interior chamber 21. Wall 43, however, has at least one portion 44 which is opposite end face 34 of sensor shaft 32 and which is formed from a flexible membrane which is permeable to the analyte. The membrane can be formed from a poly (organo)siloxane, for example. The analyte can thus diffuse out of the medium M through membrane 44 to end face 34 of sensor shaft 32 and reach permeable region 35 of sensor 3 and penetrate through it into the interior chamber of sensor 3 at distal end portion 33 of sensor shaft 32. Wall 43 is preferably configured in such a way that portion 44 of wall 43 is pre-stressed against end face 34 of distal end portion 33 of sensor shaft 32 and fits closely thereto when the sensor 3 is arranged in sensor receptacle 4 as intended and fixed there by means of the threads 31, 43.

In all embodiments, sensor 3 can in principle have a sleeve 36 at distal end section 33 of sensor shaft 32, to which permeable region 35 is fixed or which is designed for fixing permeable region 35 to sensor 3, wherein sleeve 36 can be detachably connected to a base 37 of sensor shaft 32, for example, by means of a screwed connection. Sleeve 36 can have an optical layer with a chromophore behind permeable region 35 for detecting the analyte, or other functional components for detecting the analyte.

Figures 2A, 2B, 2C:
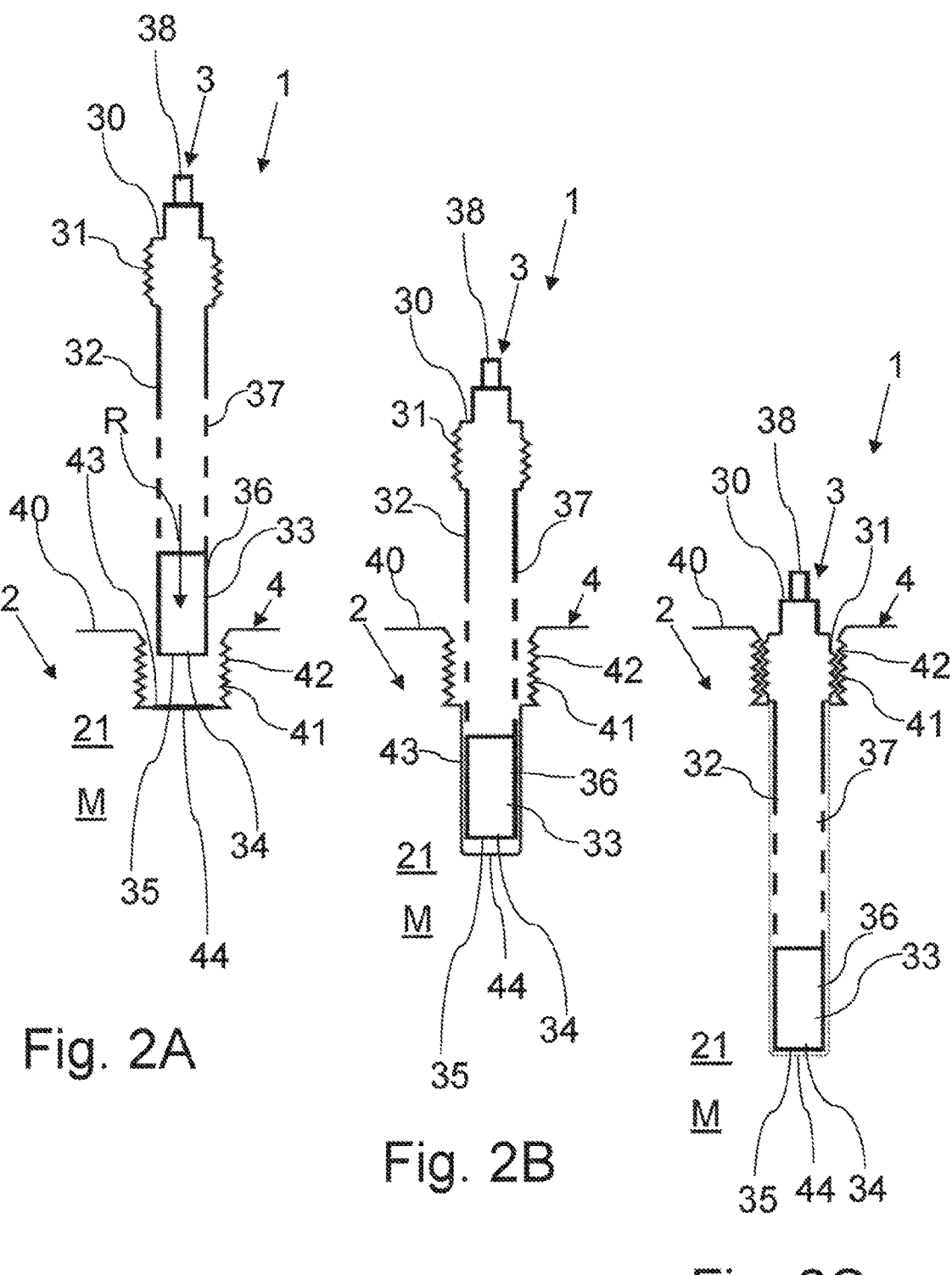
FIGS. 2A-2C show the process of arranging a sensor in a sensor receptacle of a single-use bioreactor according to an embodiment of the invention.

FIGS. 2A to 2C show the process of arranging sensor 3 in a sensor receptacle 4 of single-use bioreactor 2, which is suitable in particular for sensors 3 with a comparatively short sensor shaft 32.

In this case, sensor receptacle 4 has an expandable wall 43, which substantially closes flange 40 toward interior chamber 21 and does not protrude into interior chamber 21 of single-use bioreactor 2. Wall 43, including portion 44 of wall 43 which is intended to be opposite end face 34 of sensor shaft 32, can be formed completely from a flexible or expandable membrane, which may consist of a poly(organo) siloxane, for example.

When arranging sensor 3 in sensor receptacle 4, sensor shaft 32 is inserted with distal end portion 32 in front into flange 40, wherein end face 34 of sensor shaft 32 expands expandable wall 43 of the sensor receptacle in an insertion direction R or in the direction of the longitudinal axis of sensor shaft 32 (cf. FIG. 2B). In this case, wall 43 of sensor receptacle 4 comes into close contact with end face 34 or with permeable region 35 of sensor 3 (cf. FIG. 2C). The expanded state of wall 43 is maintained due to the interlocking threads 31, 42 of sensor 3 and flange 40.

The invention has been described here with reference to a screwed connection between sensor 3 and flange 40.

However, alternatively configured fastening regions of sensor 3 or of flange 40 are also conceivable, which allow a detachable force-fitting and/or form-fitting connection between sensor 3 and flange 40.

Figures 3A, 3B, 3C:
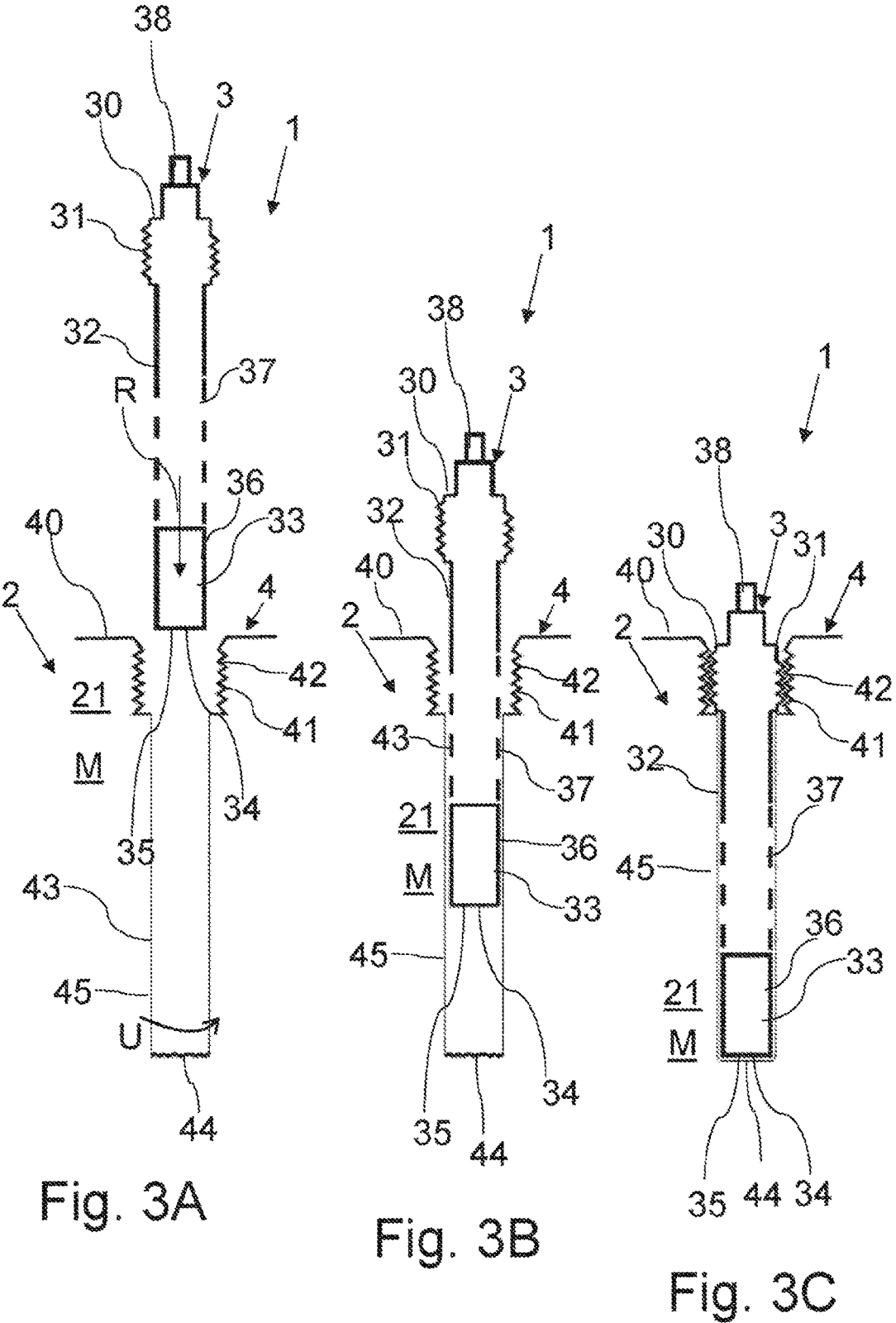
FIGS. 3A-3C show the process of arranging a sensor in a sensor receptacle of a single-use bioreactor according to a further embodiment of the invention.

FIGS. 3A to 3C show the process of arranging a sensor 3 in a further variant of sensor receptacle 4, which is suitable in particular for sensors 3 having a comparatively long sensor shaft 32.

In this case, wall 43 of sensor receptacle 4 has a rigid wall portion 45 which extends in a circumferential direction U of wall 43 and which is connected via a circumferential end to a membrane 44 which is flexible in comparison with the wall portion and which may be formed from a poly(organo) siloxane, for example.

The invention claimed is:

1. A sensor receptacle for receiving a sensor for a single-use bioreactor, such that an interior chamber of the single-use bioreactor is separated from the sensor and a sterile state of the single-use bioreactor is maintained, wherein the sensor receptacle further comprises:

a circumferential flange designed to be fixed to a reactor wall of the bioreactor, wherein the flange has a fastening region comprising an inside thread provided on a circumferential inner side of the flange and configured to receive an outside thread of a fastening region of a sensor housing of the sensor to produce a detachable, force-fitting and/or form-fitting connection between the flange and the sensor housing, a wall of the sensor receptacle, which wall is connected to the flange and which is set up and provided for separating the sensor from the interior chamber of the single-use bioreactor, wherein the wall is designed in such a way that an end face of a distal end portion of a sensor shaft of the sensor bears against a portion of the wall of the sensor receptacle, when the sensor is arranged in the sensor receptacle and the fastening region of the sensor housing is connected to the fastening region of the flange as intended, wherein at least the portion of the wall of the sensor receptacle is formed from a flexible membrane which is permeable to an analyte to be measured by means of the sensor in such a way that the analyte can pass through the flexible membrane to a region, permeable to the analyte, of the end face of the distal end portion of the sensor shaft.

2. A bioreactor system, comprising:

a pre-sterilized single-use bioreactor having a reactor wall which surrounds an interior chamber of the single-use bioreactor, the interior chamber being designed to receive a fluid medium;

a sensor being designed to detect a gaseous analyte present in the medium or an analyte dissolved in the medium, the sensor having a sensor housing with a fastening region and a sensor shaft, the sensor shaft having a distal end portion with an end face which has a region which is permeable to the analyte;

the sensor receptacle of claim 1 connected to the reactor wall and designed to receive the sensor, such that the sterility of the single-use bioreactor is maintained, the sensor receptacle having the circumferential flange via which the sensor receptacle is fixed to the reactor wall, the flange having the fastening region configured to engage in a releasable as well as the force-fitting and/or form-fitting connection with the fastening region of the sensor housing and the sensor receptacle having the wall connected to the flange which wall, together with the sensor shaft, protrudes into the interior chamber of the single-use bioreactor and thus separates the sensor from the interior chamber when the sensor is arranged in the sensor receptacle and is connected to the fastening region of the flange of the sensor receptacle by means of its fastening region as intended.

3. The bioreactor system according to claim 2, wherein the sensor receptacle is configured in such a way that the portion of the wall is pre-stressed against the end face of the distal end portion of the sensor shaft when the sensor is arranged in the sensor receptacle and the fastening region of the sensor housing is connected to the fastening region of the flange as intended.

4. The bioreactor system according to claim 3, characterized in that the wall of the sensor receptacle is designed to be expandable, such that the wall is expanded in a direction in which the sensor shaft can be inserted into the sensor receptacle when the sensor is arranged in the sensor receptacle and the fastening region of the sensor housing is connected to the fastening region of the flange as intended.

5. The bioreactor system according to claim 4, wherein the wall is completely formed by the flexible membrane.

6. The bioreactor system according to claim 2, wherein the wall of the sensor receptacle has a rigid wall portion, which extends in a circumferential direction and is connected to the portion of the wall, wherein the portion of the wall is formed by the flexible membrane.

7. The bioreactor system according to claim 6, wherein the flexible membrane is formed from a material selected from the group consisting of an inorganic polymer, an organic polymer, and a poly(organo)siloxane.

8. The bioreactor system according to claim 2, wherein the analyte is one of the following analytes: oxygen, $CO_2$, $SO_2$, $H_2O_2$, $NO_x$, a halogenated hydrocarbon.

9. The bioreactor system according to claim 2, wherein the sensor shaft has a sleeve at the distal end portion of the sensor shaft, on which sleeve the permeable region is fixed, or which is designed for fixing the permeable region to the sensor, wherein the sleeve can be detachably connected to a base of the sensor shaft.

10. The bioreactor system according to claim 2, wherein the reactor wall is designed to be rigid or at least partially rigid, or in that the reactor wall is designed to be flexible.

11. The bioreactor system according to claim 2, wherein the portion of the wall of the sensor receptacle is formed from a material which does not have a chromophore.

12. The bioreactor system according to claim 2, characterized in that the wall of the sensor receptacle is designed to be expandable, such that the wall is expanded in a direction in which the sensor shaft can be inserted into the sensor receptacle when the sensor is arranged in the sensor receptacle and the fastening region of the sensor housing is connected to the fastening region of the flange as intended.

13. The bioreactor system according to claim 2, wherein the wall is completely formed by the flexible membrane.

14. The bioreactor system according to claim 2, wherein the flexible membrane is formed from a material selected from the group consisting of: an inorganic polymer, an organic polymer, and a poly(organo) siloxane.

15. A method for measuring an analyte in a medium using the bioreactor system of claim 2, said method comprising the steps of:

providing the pre-sterilized single-use bioreactor, arranging the separate sensor in the sensor receptacle wherein the fastening region of the sensor housing is connected in a force-fitting and/or form-fitting manner to the fastening region of the flange of the sensor receptacle in such a way that the end face of the distal end portion of the sensor shaft bears against the portion of the wall of the sensor receptacle, and measuring a concentration of the analyte of the medium located in the interior chamber by means of the sensor.

* * * * *